United States Patent [19]
Armitage et al.

[11] Patent Number: 5,998,180
[45] Date of Patent: Dec. 7, 1999

[54] **NITRILASE FROM *RHODOCCUS RHODOCHROUS* FOR CONVERTING ACRYLONITRILE DIRECTLY TO ACRYLIC ACID**

[75] Inventors: Yvonne Christine Armitage, Huddersfield; Jonathan Hughes, Brighouse; Neil Andrew Webster, West Yorkshire, all of United Kingdom

[73] Assignee: Ciba Specialty Chemicals Water Treatments Limited, Bradfort, United Kingdom

[21] Appl. No.: 08/930,823

[22] PCT Filed: Dec. 12, 1996

[86] PCT No.: PCT/GB96/03080

§ 371 Date: Feb. 24, 1998

§ 102(e) Date: Feb. 24, 1998

[87] PCT Pub. No.: WO97/21805

PCT Pub. Date: Jun. 19, 1997

[30] Foreign Application Priority Data

Dec. 12, 1995 [GB] United Kingdom .................. 9525372

[51] Int. Cl.$^6$ .............................. C12P 7/60; C12N 9/78; C12N 1/20
[52] U.S. Cl. ....................... 435/138; 435/227; 435/252.2
[58] Field of Search ................................ 435/227, 138, 435/252.2

[56] References Cited

U.S. PATENT DOCUMENTS

| | | | |
|---|---|---|---|
| 4,248,968 | 2/1981 | Watanabe et al. | 435/129 |
| 4,629,700 | 12/1986 | Prevatt et al. | 435/128 |
| 4,908,313 | 3/1990 | Satoh et al. | 435/129 |
| 5,135,858 | 8/1992 | Yamada et al. | 435/106 |
| 5,629,190 | 5/1997 | Petre et al. | 435/227 |

FOREIGN PATENT DOCUMENTS

| | | |
|---|---|---|
| 0 187 680 A2 | 7/1986 | European Pat. Off. . |
| 0 188 316 A2 | 7/1986 | European Pat. Off. . |
| 0 307 926 A2 | 3/1989 | European Pat. Off. . |
| 0 444 640 A2 | 9/1991 | European Pat. Off. . |
| 63-2596 | 1/1988 | Japan . |
| 4341158 | 11/1992 | Japan . |
| 8173152 | 7/1996 | Japan . |
| 1 475 540 | 6/1977 | United Kingdom . |
| 95/04828 | 2/1995 | WIPO . |
| 97/06248 | 2/1997 | WIPO . |

OTHER PUBLICATIONS

Zabaznaya et al., Appl. Biochem. Microbiol., 34(4), "Selection of Strains Transforming Acrylonitrile and Acrylamide into Acrylic Acid", pp. 341–345, Jul. 1998.

Thompson et al., Chem. Brit., 24(9), "Microbial Biotransformations of Nitriles: Potential Application in Waste Treatment", pp. 900–902, Sep. 1988.

Zhao et al., J. Shandong Univeristy, 29(2), "Production of Acrylic Acid by Microbial Conversion of Acrylonitrile", pp. 217–223, Jun. 1994.

Battistel et al., Biotechnol. Lett., 19(2), "Enzymic Decontamination of Aqueous Polymer Emulsions Containing Acrylonitrile", pp. 131–134, Feb. 1997.

Kobayashi et al., Trends Biotechnol., 10(11), "Enzymatic Synthesis of Acrylamide: a Success Story Not Yet Over; Acrylamide Production Using Nitrilase, Nitrile–hydratase and Amidase of e.g. *Rhodococcus rhodochrous*", pp. 402–408, Nov. 1992.

Yamamoto et al., Agric. Biol. Chem., 55(6), "Purification and Characterization of Nitrilase Responsible for the Enantioselective Hydrolysis from Acinetobacter sp. AK 226", pp. 1459–1466, Jun. 1991.

Kobayashi et al., J. Bacteriol., 172(9), "Purification and Characterization of a Novel Nitrilase of *Rhodococcus Rhodochrous* K22 That Acts on Aliphatic Nitriles", pp. 4807–4815, Sep. 1990.

DiGeronimo et al., Appl. Environ. Microbiol., 31(6), "Metabolism of Acetonitrile and Proprionitrile by *Nocardia rhodochrous* LL100–21", pp. 900–906, Jun. 1976.

Zhao et al., in Chemical Abstracts, vol. 121, No. 21, Nov. 21, 1994, Abst #253,825.

Kobayashi et al. in Chemical Abstracts, vol. 113, No. 19, Nov. 5, 1990, Abst. #167,832.

Archives of Microbiology, vol. 155, 1990, (b), pp. 13–17, Toru Nagasawa et al.

Applied Microbiology and Biotechnology, vol. 34, 1990, (a), pp. 322–324, Toru Nagasawa et al.

Biotechnology and Applied Biochemistry, vol. 11, 1989, pp. 581–601, Goldlust et al.

Kobayashi et al. Journal of Bacteriology, vol. 172, No. 9, Sep. 1990, pp. 4807–4815.

Biotechnology and Applied Biochemistry, vol. 15, 1992, David E. Stevenson et al, pp. 283–302.

*Primary Examiner*—Jon P. Weber
*Attorney, Agent, or Firm*—David R. Crichton

[57] ABSTRACT

Nitrilase enzymes are provided which have Km at pH 7.0 for acrylonitrile of 500 $\mu$M or below. The enzymes also have Ki at pH 7.0 for ammonium acrylate of at least 100 mM. In particular, the nitrilases have a value of the ratio of the said Ki to the said Km of at least 200. Particularly preferred nitrilases are obtainable from the microorganisms *Rhodococcus rhodochrous* NCIMB 40757 or NCIMB 40833. These nitrilases can be used in processes of converting acrylonitrile to ammonium acrylate in aqueous or vapor form and for detecting low levels of nitrile in aqueous or vapor form.

15 Claims, No Drawings

NITRILASE FROM RHODOCCUS RHODOCHROUS FOR CONVERTING ACRYLONITRILE DIRECTLY TO ACRYLIC ACID

This application is a 371 application of PCT Application PCT/GB 96/03080, filed Dec. 12, 1996.

This invention relates to enzymatic processes for the production of ammonium acrylate and to novel micro-organisms and enzymes useful in these processes.

Acrylic acid (or its salts) is generally made by a single stage chemical conversion from propylene oxide or a two-stage conversion from acrylonitrile, through acrylamide sulphate intermediate. This chemical conversion can give a product containing undesirable impurities from side reactions including the formation of some dimeric acrylic acid, which tends to form when the product acrylic acid is present in high concentration under the conditions of manufacture.

The use of an amidase for converting acrylamide to acrylic acid (as the ammonium salt) has frequently been described in the literature. It has been described primarily for converting residual monomer impurity in an acrylamide polymer to ammonium acrylate but it has also been proposed that it would be desirable to use an amidase for the commercial production of ammonium acrylate from acrylamide.

Processes of making acrylamide from acrylonitrile by a nitrile hydratase are known and are described in, for instance, EP-A-307,926 and Appl. Microbiol. Biotechnol. 1993, 40, pages 189 to 195. This latter article shows that a nitrile hydratase can be obtained from, inter alia, R rhodochrous J1. EP-A-188316 describes the conversion of acrylonitrile to acrylamide using a nitrile hydratase. One nitrile hydratase is obtained from Rhodococcus sp.S-6. WO95/04828 describes nitrile hydratases, one of which, from Comamonas NI1, is illustrated as converting acrylonitrile to acrylamide. Such processes, if applied to the production of ammonium acrylate, would involve two stages, namely the production of acrylamide as a first stage and the hydrolysis of this to acrylic acid as a second stage. Use of a two step process generally gives rise to the presence of two types of impurity. These are unreacted starting material from the first stage and unreacted product of the first stage, which is the starting material for the second stage.

A further conversion of nitrile to its corresponding acid is described in GB 1,475,540. This conversion is carried out on various nitriles which include acrylonitrile by particular strains of bacteria. These are of genera Bacillus, Bacteridium, Micrococcus or Brevibacterium. The exemplified conversions are on lactonitrile, glycinonitrile, amino propionitrile hydrochloride, amino-3-propionitrile and α-amino-γ-methyl thiobutyronitrile. We believe that the microorganisms carried out the hydrolysis by producing a nitrile hydratase enzyme which converts the nitrile to an amide and an amidase enzyme which subsequently converts the amide to an acid.

It would be desirable to be able to produce ammonium acrylate by an enzymatic, commercially convenient, process in a single stage from acrylonitrile, using an acrylonitrilase.

Processes of converting acrylonitrile to ammonium acrylate using a nitrilase have been described in the literature, for instance EP-A-187,680, JP-B-63-2596 and Appl Microbiol. Biotechnol. 1990, 34, pages 322 to 324, which uses a nitrilase derived from R rhodochrous J1 (the same micro-organisms discussed in EP-A-307,926 above), and in EP-A-444,640 which also describes a nitrilase from R rhodochrous J1 as being preferred.

The use of R rhodochrous K22 is described in J. Bacteriol. 172, 9, pages 4807 to 4815 for the process of converting acrylonitrile to ammonium acrylate.

Nitrilase from Fusarium oxysporum f.sp. melonis is demonstrated acting on up to 60 mM acrylonitrile to produce acrylic acid in Biotech. Appl. Biochem., 1989, 11, pages 581 to 601.

Stevenson et al in Biotech. and Appl. Biochem. 15, 283–302 (1992) describe studies on a nitrilase produced by Rhodococcus ATCC 39484. The enzyme is most effective for hydrolysis of aromatic nitrites and shows little or no activity for many aliphatic nitriles such as acrylonitrile. The enzyme is said to have a pH optimum of 7.5, to be totally inactivated outside the pH range 5.0 to 9.0 and irreversibly inactivated by preincubation above 40° C. The enzyme also showed activation in the presence of substrates, in particular benzonitrile. The authors of the article believe this is due to subunit aggregation.

Unfortunately none of the known processes using nitrilase is commercially satisfactory. For instance the process described in Appl. Microbiol. Biotechnol. 34, 1990 pages 322 to 324 shows that R rhodochrous J1 required a pH of 7.8 for optimum activity, underwent slight inactivation between 30 and 50° C., and nearly total deactivation at 60° C., was inhibited by concentrations of acrylonitrile above 200 mM and was inhibited by the product (ammonium acrylate) which was formed. There is inadequate data in that article to indicate the Km value of the nitrilase produced by the micro-organism with respect to acrylonitrile or its Ki value with respect to ammonium acrylate but the Km value for R rhodochrous K22 is reported in the J. Bacteriol article above as being 1.14 mM. The value of 17 mM had been reported for the acrylonitrilase in Biotech. Appl. Biochem., 1989, 11, pages 581 to 601, and around 4 to 6% of acrylamide was reported as having been formed during the reaction.

It would be desirable to be able to obtain ammonium acrylate in good yield at high concentration in an economic process. It would be desirable to provide micro-organisms and enzymes that permit this.

Nitrilase having unusual and very desirable activity has been identified. The nitrilase can therefore be used to catalyse the reaction from acrylonitrile to ammonium acrylate, either in whole-cell form or as an extracted enzyme. It can also be used to catalyse analogous reactions of other nitrites, for instance adiponitrile.

A novel nitrilase is characterised by having Km for acrylonitrile below 500 $\mu$M. Throughout this specification Km refers to Km measured at pH 7.0. Km is measured under conditions under which the enzyme exhibits Michaelis-Menten kinetics. In particular we use the conditions of Example 6 below. A preferred nitrilase on which we have conducted initial experiments has Km for acrylonitrile 30.6 $\mu$M in whole cell form and we anticipate that the application of standard techniques and selection procedures, eg, those described for amidase in Silman et al., (1989) J. Gen. Microbial., 135 3153–3164 and those described for lactate dehydrogenase by Wagner (1990) Tibtech., 8, 263–270 will yield nitrilase having Km values up to 60 or 100, or perhaps 300 $\mu$M, and Km values down to. 9.4 and even 3.8 $\mu$M.

A major advantage of the novel nitrilase having Km below 500 $\mu$M lies in the fact that it can therefore be effective at very low levels of nitrile substrate. It is conventional to carry out enzyme-catalysed reactions using a concentration of substrate which is around ten times Km. Thus using the novel nitrilase of the invention it is possible to carry out conversion of acrylonitrile to ammonium acrylate using concentrations of acrylonitrile 500 $\mu$M or below, even as low as 300 $\mu$M, often 40 to 100 $\mu$M. This is advantageous because it enables continuous production of ammonium acrylate by a process having levels of acrylonitrile of 300 ppm or less in the reactor and consequently in the ammonium acrylate product. The novel nitrilase of the invention may also be used in processes in which the acrylonitrile substrate concentration is greater than 300 ppm and may also be used in batch or fed batch processes.

A further advantage of the low Km of the enzyme of the invention is the excellent scavenging ability of the enzyme. Because the nitrilase is active at very low concentrations of acrylonitrile it can scavenge very low levels of residual acrylonitrile from for instance an ammonium acrylate product containing residual acrylonitrile.

It is also advantageous to be able to work at very low nitrile levels because acrylonitrile and other nitriles have a tendency to deactivate nitrilases when present at high concentration. Known enzymes of higher Km have hitherto been limited in that they require a certain minimum level of nitrile for effective activity but this level is high enough to lead to deactivation. The nitrilase of the invention is capable of acting effectively to produce ammonium acrylate or other salt from concentrations of acrylonitrile or other nitrile which are low enough to avoid a significant deactivation of the enzyme.

A novel nitrilase of the invention is characterised by having Ki for ammonium acrylate of at least 100 mM, preferably at least 150 or 200, more preferably at least 250 mM. Throughout this specification Ki refers to Ki measured at pH 7.0. The enzyme exhibits Michaelis-Menten kinetics under the conditions of measurement. Preferably measurement is under the conditions given in Example 7 below. A preferred nitrilase on which we have conducted initial experiments has Ki for ammonium acrylate which we have estimated to be 309 mM. It is envisaged that standard techniques and selection procedures, eg mutagenesis, will yield nitrilase having Ki for ammonium acrylate up to 300 mM or even 800 mM or greater.

The high Ki value of the nitrilase of the invention is advantageous because it allows the enzyme to catalyse reactions of acrylonitrile which produce high concentrations of ammonium acrylate (10% w/v or more, for instance up to 30 or 40%). In such reactions the degree of inhibition of the action of the enzyme by the product is low.

A novel nitrilase of the invention is characterised by having a ratio (Ki for ammonium acrylate)/(Km for acrylonitrile) of at least 200. Preferably the ratio is at least 300, more preferably at least 500, in particular at least 1000. Nitrilases of the invention can have a ratio Ki/Km of at least 5000, even 9000 or greater and a nitrilase on which we have conducted initial experiments has a value of this ratio of greater than 10000.

An advantage of a high value of the specified ratio is that the nitrilase is capable of catalysing hydrolysis of very low levels of nitrile, such as acrylonitrile, in conditions in which there exists high concentration of the corresponding salt, for instance ammonium acrylate.

A novel nitrilase is characterised by having, at pH 6.8, a specific acrylonitrilase activity which is at least 80%, and preferably at least 95%, of its activity at optimum pH. Optimum pH is the pH at which the nitrilase has maximum specific acrylonitrilase activity. Its optimum pH is generally in the range 6.5 to 7, often around 6.8, and thus the nitrilase has the advantage that it has optimum activity at the natural pH of ammonium acrylate. Accordingly buffering or constant monitoring and adjustment is unnecessary.

A novel nitrilase of the invention is characterised by having improved temperature stability as follows: it retains at 50° C. at least 80% of its acrylonitrilase activity at 25° C. Activity is measured by incubation of the cells in water at the required temperature for 5 minutes and then adding acrylonitrile at a concentration of 50 mM and monitoring conversion to ammonium acrylate for 15 minutes. Preferably the nitrilase also retains at 55° C. and at 60° C. at least 80% of its acrylonitrilase activity at 25° C. The activity at 50° C., 55° C. and 60° C. may be even higher than the activity at 25° C., for instance at least 100%, or even 200% or 300% of activity at 25° C.

A novel nitrilase of the invention retains at least 80% of its original specific acrylonitrilase activity after being immobilised in cross-linked polyacrylamide beads as follows:

A paste consisting of cells containing nitrilase is suspended in chilled buffer and added to a mixture of acrylamide monomer and methylene bis acrylamide cross-linker in chilled buffer. The water soluble component of a redox initiator system is added immediately. The mixture is then transferred to a stirred resin pot containing chilled mineral oil and surfactant and the second redox initiator component, soluble in both liquid phases, is added to initiate the polymerisation. Upon polymerisation the cells are entrapped in cross-linked polymer beads. Preferably the nitrilase when immobilised in cross-linked polyacrylamide beads under these conditions retains at least 90%, preferably at least 95%, more preferably substantially all, of its immobilised acrylonitrilase specific activity after being dried to 12% moisture at 60° C. and/or freeze-dried at 0.1 mbar for 24 hours. By "immobilised specific activity" we mean the specific activity of the enzyme which is shown after it has been immobilised in cross-linked polyacrylamide beads. Preferably also the specific acrylonitrilase activity of the nitrilase immobilised in cross-linked polyacrylamide beads and optionally dried and stored at 20° C. for 17 days is at least 90%, preferably at least 95%, more preferably substantially all, of the immobilised specific activity.

Thus the nitrilase of this aspect of the invention is highly chemically and physically stable. This renders it highly suitable for incorporation into beads of polymeric material. It is known to immobilise enzymes in whole cell form into beads of cross-linked polymeric material, in particular polyacrylamide, in order to place them in conveniently usable form. The nitrilase of the invention is not denatured (i.e. does not undergo significant reduction in specific activity) when incorporated into this form. Furthermore, after the nitrilase has been incorporated into cross-linked polyacrylamide beads, preferably the activity of the enzyme in these beads is not significantly reduced on drying or storage of the beads.

A novel nitrilase of the invention is characterised by having a half life as measured in an aqueous solution containing 125 to 175 mM acrylonitrile and 2,475 to 2,525 mM ammonium acrylate of at least 5 days, preferably at least 7 days, more preferably at least 7.5 days. The exact content of acrylonitrile and ammonium acrylate may vary during the test but is always kept within the specified concentration limits. Acrylonitrile will be converted to ammonium acrylate by the nitrilase and the acrylonitrile concentration will thus reduce progressively. When the concentration reaches the lower limit of 125 mM, additional acrylonitrile is added to raise the concentration to the upper limit of 175 mM. Similarly the amounts of ammonium acrylate are allowed to vary between the specified levels, with adjustment of ammonium acrylate concentration to prevent concentration going above the specified maximum of 2525 mM. A particular microorganism on which we have conducted preliminary experiments has produced a nitrilase which has a half life under these conditions of 7.6 days and we envisage that enzyme having a half-life of at least 10 to 15 days could be produced.

This advantageous half life indicates that the nitrilase of the invention has high stability to denaturing by both substrate and product (acrylonitrile and ammonium acrylate), in particular high concentrations of product.

The long half life of the acrylonitrilase enzyme of this aspect of the invention is particularly advantageous for long-term commercial use. A batch of enzyme can be added to a reactor and remain there for several days, for instance 10 or more or even up to 20 or 30 days, without the necessity for adding further enzyme to the reactor to replace denatured enzyme.

The nitrilases of the invention preferably have the property of increasing their specific activity when exposed to acrylonitrile and/or ammonium acrylate. Preferably they show an increase in specific activity of at least 1.7 times, preferably at least 2 or 3 times and usually not more than 10 times, following incubation for 1 to 3 hours in the presence of 4 to 175 mM aqueous acrylonitrile and/or 1.2 to 2.5 M aqueous ammonium acrylate. The exact content of acrylonitrile and ammonium acrylate may vary during the test but is always kept within the specified concentration limits. Acrylonitrile will be converted to ammonium acrylate by the nitrilase and the acrylonitrile concentration will thus reduce progressively. When the concentration reaches the lower limit of 125 mM, additional acrylonitrile is added to raise the concentration to the upper limit of 175 mM. Similarly the amounts of ammonium acrylate are allowed to vary between the specified levels, with adjustment of ammonium acrylate concentration to prevent concentration going above the specified maximum of 2525 mM.

Improved nitrilases of this type thus have the important advantage that they increase in activity when exposed to the reaction environment in which they are used.

Although the invention provides novel nitrilases having any one of the properties discussed above, preferably the nitrilase of the invention possesses more than one of the specified properties. In particular it is preferred that the nitrilase of the invention possesses a Km for acrylonitrile of below 500 $\mu$M and, more preferably, also a Ki for ammonium acrylate of at least 100 mM.

Particularly preferably the nitrilase also possesses a value of the ratio (Ki for ammonium acrylate)/(Km for acrylonitrile) of at least 200.

More preferably the acrylonitrilase of the invention has, in addition to these Km, Ki and Ki/Km properties, at least two of the other properties specified above, more preferably all properties specified above.

We have isolated a new microorganism, a strain of R. rhodochrous which is capable of producing a nitrilase which possesses all the above properties. This microorganism has been deposited at NCIMB on Aug. 8, 1995 in accordance with the provisions of the Budapest Treaty under accession number NCIMB 40757 at the National Collections of Industrial and Marine Bacteria, 23 St. Machar Drive, Aberdeen AB2 1RY, Scotland, UK (by Jonathan Hughes of Allied Colloids Ltd., PO Box 38, Low Moor, Bradford, West Yorkshire, BD12 OJZ, England, and on behalf of Allied Colloids Ltd.). We have also newly deposited on Dec. 11, 1996 a strain of *Rhodococcus rhodochrous* NCIMB 40833 at the National Collections of Industrial and Marine Bacteria, 23 St. Machar Drive, Aberdeen AB2 1RY, Scotland, UK (by Jonathan Hughes of Allied Colloids Ltd., PO Box 38, Low Moor, Bradford, West Yorkshire, BD12 OJZ, England, and on behalf of Allied Colloids Ltd.). This also possesses all the above properties and is referred to below as "the newly deposited strain".

Accordingly, a further aspect of the invention provides the microorganism *Rhodococcus rhodochrous* NCIMB 40757 or the newly deposited NCIMB 40833, or a mutant of either capable of producing a nitrilase.

The invention also provides a novel nitrilase enzyme obtainable by culturing *Rhodococcus rhodochrous* NCIMB 40757 or the newly deposited strain NCIMB 40833.

The strain deposited under NCIMB 40757 showed the following results on analysis:

The cell wall diamino acid is meso DAP. The fatty acid profile shows the following acids in the indicated percentages:

| | |
|---|---|
| tetradecanoic | 2.1% |
| pentadecanoic | 2.8% |
| hexadecenoic | 24.7% |
| hexadecanoic | 25.9% |
| heptadecenoic | 6.2% |
| heptadecanoic | 3.1 |
| octadecenoic | 25.0% |
| octadecanoic | 1.9% |
| tuberculostearic | 7.0%. |

Biochemical testing gave the following results:
Decomposition of:

| | |
|---|---|
| Adenine | − |
| Tyrosine | + |
| Urea | − |

Growth in Presence of:

| | |
|---|---|
| 5% NaCl | + |
| Dextrose azide | (+) |

Growth on sole carbon sources:

| | | |
|---|---|---|
| Inositol | (+) | |
| Maltose | + | |
| Mannitol | + | |
| Rhamnose | − | |
| Sorbitol | + | |
| m-hydroxybenzoic acid | + | |
| Sodium adipate | + | |
| Sodium benzoate | + | |
| Sodium citrate | + | |
| Sodium lactate | + | |
| Sodium glutamate | − | |
| L-tyrosine | + | |
| Glycerol | + | |
| Trehalose | + | |
| p-hydroxybenzoic acid | + | |
| D-mannose | + | |
| Acetamide | + | |
| D-galactose | (+) | (+) weak positive |

Enzyme Tests: Rosco discs. 4 hours. 37° C.

| | |
|---|---|
| α-glucosidase | − |
| Cysteine arylamidase | − |
| Valine arylamidase | − |

Nitrilase obtained from R rhodochrous NCIMB 40757 and NCIMB 40833 and all nitrilases of the invention may be used in a process of conversion of a nitrile to the corresponding ammonium salt. Thus according to a further aspect of the invention we provide a process of converting a nitrile in aqueous solution to the corresponding ammonium salt in the presence as hydrolysis catalyst of a nitrilase of the invention, preferably nitrilase obtainable by culturing R rhodochrous NCIMB 40757 or NCIMB 40833.

Preferably the nitrile is acrylonitrile and the corresponding ammonium salt therefore ammonium acrylate, and the process will be discussed below in terms of acrylonitrile and ammonium acrylate. Other nitriles may be converted in the process, for instance adiponitrile, methacrylonitrile, α-aminonitriles, acetonitrile, n-butyronitrile, iso-butyronitrile, n-valeronitrile, benzonitrile, cyanopyridine, malononitrile, succinotrile, fumaronitrile, chloracetonitrile and β-hydroxypropionitrile.

The various unique properties of the nitrilases of the invention allow processes to be carried out in which a continuously low concentration of acrylonitrile is converted to a continuously high concentration of ammonium acrylate.

Thus in the invention it is possible to convert an aqueous solution of acrylonitrile at 3.0 mM or below, often 2.0 mM or below, and even 1.5 mM or below to aqueous ammonium acrylate at a concentration of at least 5%, often at least 8 or 10%. It is also possible to convert a solution of aqueous acrylonitrile at a concentration of 3.0 to 6.0 mM, often 4.0 to 5.0 mM, to aqueous ammonium acrylate at a concentration of at least 20%, often at least 25 or 30% and even up to 40% or more. Maximum ammonium acrylate concentration is usually around 48 to 50% (W/V).

The processes of the invention are generally carried out at a temperature of 5 to 70° C. preferably 20 to 60° C. Conditions of pH are usually 3 to 9.5, preferably 5 to 9, more preferably 6 to 8.

When the above conversions are taking place the process of the invention may be conducted as a continuous process. That is, acrylonitrile is continuously fed into a reactor to maintain a steady acrylonitrile concentration and reaction solution containing a steady concentration of ammonium acrylate is continuously drawn off.

Water is also required as a reactant. Water may be present in the full amount required from the beginning of the reaction. Alternatively, it may be fed in to the reactor during the reaction. For instance, the acrylonitrile may be fed in the form of a solution, usually a saturated solution, that is about 7% weight/weight. Alternatively water may be fed in separately and the acrylonitrile is fed in the neat form or as a solution.

Continuous reactions of this type may be carried out in for instance a continuous stirred tank reactor, fluidised bed reactor, packed bed reactor, draw-fill type reactor or plug flow reactor.

The process under the above conditions may also be carried out as a fed batch process. In a fed batch process acrylonitrile concentration is allowed to decrease as a result of conversion to ammonium acrylate until it reaches a predetermined minimum level. At this point further acrylonitrile is added to the reaction mixture to raise concentration to a predetermined maximum level. Acrylonitrile is then allowed to decrease again to the predetermined minimum level. When ammonium acrylate level reaches a predetermined maximum level, the reaction mixture is collected and a new batch of acrylonitrile added to the reactor and enzyme. As with continuous processes, water may be fed into the reactor during the reaction if required.

Alternatively, the nitrilases of the invention may be used to catalyse conversion of acrylonitrile to ammonium acrylate in a batch process. That is, a relatively high concentration of acrylonitrile is used as starting material. The acrylonitrilase is allowed to convert this acrylonitrile to ammonium acrylate with no further addition of starting material. When conversion of acrylonitrile is finished the reaction mixture is collected and used and a new reaction mixture is provided.

Preferably however the process of the invention is a continuous or fed batch process. Especially preferred processes are described in our co-pending international application no. . . . filed today (reference PRL03626WO) claiming priority from GB 9525374.6 and GB 9525372.0.

Such processes comprise making an aqueous solution containing at least 30 wt % (meth) acrylic acid or salt thereof and below 0.2% (meth) acrylonitrile comprising providing water and (meth) acrylonitrile in an amount sufficient to provide, upon hydrolysis, a concentration of (meth) acrylic acid or salt thereof of at least 30 wt % and providing during the process, in contact with the (meth) acrylonitrile, an enzyme which converts (meth) acrylonitrile to ammonium (meth) acrylate and which has Km for (meth) acrylonitrile below 500 $\mu$M and Ki for ammonium (meth) acrylate above 100,000 $\mu$M, allowing hydrolysis of the (meth) acrylonitrile to occur until the reaction solution has a concentration of (meth) acrylonitrile of below 0.2% and a concentration of ammonium (meth) acrylate of above 30%, and recovering a solution of ammonium (meth) acrylate of above 30% and acrylonitrile of below 0.2%. In these processes (meth) acrylonitrile may be subjected to chemical hydrolysis to provide a solution containing ammonium (meth) acrylate and acrylonitrile and the resultant solution is then contacted with the said enzyme and hydrolysis of the (meth) acrylonitrile is allowed to occur until the reaction solution has a concentration of (meth) acrylonitrile of below 0.2%. Alternatively substantially all the hydrolysis of the (meth) acrylonitrile can be by enzymatic hydrolysis with the said enzyme.

These processes may be carried out as a one-stage or a two-stage process. One-stage processes comprise making an aqueous solution containing at least 30% by weight ammonium (meth) acrylate and below 0.1% (meth) acrylonitrile by a process comprising charging a reactor during the process with an enzyme for converting (meth) acrylonitrile to ammonium (meth) acrylate and which has Km for (meth) acrylonitiile below 500 $\mu$M and Ki for ammonium (meth) acrylate above 100 mM and with water and with (meth) acrylonitrile in an amount sufficient to provide, upon hydrolysis, an ammonium (meth) acrylate concentration of at least 30% by weight, and allowing hydrolysis to occur in the reactor until the solution in the reactor has a concentration of (meth) acrylonitrile of below 0.2% and a concentration of ammonium (meth) acrylate of above 30%. and removing this solution from the reactor.

In this preferred process the final concentration of (meth) acrylonitrile is probably below 0.1%, more preferably below 0.05%. Preferably it is below 0.03%, more preferably below 0.02 or 0.01%.

The final concentration of ammonium (meth) acrylate is at least 30% by weight, often at least 35% by weight, preferably at least 40 or 45% by weight. Maximum concentration of ammonium (meth) acrylate is usually 48 to 50 wt %, since above these levels the ammonium (meth) acrylate tends to precipitate out of solution.

In the preferred process the enzyme is included in the reaction mixture so as to provide the desired activity in the reactor. Usually the form of catalyst added to the reactor has an activity of from 50 to 100,000 nitrilase units per gram, typically 500 to 5,000 nitrilase units per gram, where one nitrilase unit is defined as conversion of acrylonitrile to ammonium acrylate at the rate of 1 $\mu$mol/min at 30° C., pH 7.0 and 50 mM acrylonitrile in 50 mM phosphate buffer. The catalyst may be in the form of bacterial cells or, more usually, immobilised in a polymer gel matrix. The catalyst having the defined activity is included in the reactor in an amount of from 1 to 50% by weight of reaction mixture.

In particular, it is preferred that enzyme is added to the reaction mixture to give an activity of 3,000 to 50,000 nitrilase units per liter of reaction mixture.

In the preferred process the full amount of required enzyme is usually charged to the reactor at the beginning of the reaction, that is before addition of (meth) acrylonitrile reactant. However, it is also possible to carry out the preferred process by adding additional enzyme during the reaction, either continuously or periodically.

Similarly, water, which is also a reactant as well as a solvent, may be included in the reactor in the full amount at the beginning of the reaction. Alternatively, it may be fed into the reactor continuously during the reaction in the same way as is possible with the (meth) acrylonitrile reactant.

The reaction is carried out in aqueous solution. Generally the only components of the aqueous solution are water enzyme (including bacterial cells, polymer matrix etc), (meth) acrylonitrile and ammonium (meth) acrylate.

The process of the invention may alternatively be a process of purification of a polymer formed from a monomer blend including acrylonitrile monomer and which contain unreacted acrylonitrile monomer by converting the unreacted acrylonitrile monomer to ammonium acrylate in the presence of acrylonitrilase catalyst of the invention. This may be carried out under conditions in which acrylonitrile monomer can be reduced to levels of below 1,000 ppm, often below 500 ppm, preferably below 300 or even 100 ppm, based on weight of polymer.

The process of the invention may be a process of purification of monomer containing residual acrylonitrile, the monomer having been obtained by any method, for instance chemical hydrolysis of acrylonitrile. In such processes the starting level of acrylamides may be up to 5%, but is normally below 2%, for instance from 0.5 to 1%.

In the process of the invention and in any other process in which it is used the nitrilase may be used in any convenient form, for instance in the pure form, having been extracted from a cultured microorganism before use as a catalyst. The extraction method used should ensure that the activity and stability of the enzyme are not lost.

It may also be used in a semi-pure form, for instance as liquid culture or a bacterial cell fraction such as intact cells or crushed cells. It may be used in the form of crude, impure enzyme solution. It may be supported or imobilised on a carrier, such as a cross-linked polymeric matrix, eg crosslinked polyvinyl alcohol or cross-linked polyacrylamide. If may be used in the form of non-swollen particles having surface-bound enzyme. Preferably it is used in the form of intact bacterial cells or supported in a cross linked polymeric matrix.

We find that for fed batch type reactions in particular it is advantageous to use enzyme in pure or semi-pure form as free cells. Use in this form avoids the necessity to immobilise the cells on a carrier but we find it does not lead to reduced stability on storage or in the reaction mixture to an excessive extent.

For continuous type processes we prefer to use enzyme in the immobilised form, since this tends to give greater long term stability in the reactor which is used. In particular, we have found that in some circumstances enzyme in immobilised form is as stable in the reaction mixture as it is on storage. Separation of catalyst from the final product also tends to be easier.

When the enzyme is being immobilised, in particular in the form of polymer beads, we find that production of polymer beads of larger size improves enzyme stability during polymerisation. In particular beads of size greater than 850 μm, preferably greater than 1 mm, are preferred.

Polymeric matrix can be produced in any manner, for instance by bead or suspension polymerisation. Addition of viscosifier to the monomer mixture can also be useful.

We find that stability of the enzyme during production is greatest at low cell loading, ie weight percentage of dry cells based on polymer matrix, in particular below 5%, preferably below 1%, for instance around 0.5 wt %. However, stability can also be achieved by using low polymerisation temperature, for instance below 30 or 20° C., often below 15° C. This can be used in combination with a higher cell loading, for instance at least 4 wt %, preferably at least 5 wt %, for instance around 6.5 or 6.8 wt %.

An advantage of the nitrilases of the invention, in particular the nitrilase produced by R. rhodochrous NCIMB 40757 and the newly deposited strain NCIMB 40833, is their ability to convert low concentrations of acrylonitrile, for instance below 18.86 mM (1,000 ppm), to high concentrations of ammonium acrylate, for instance 30%, 40% or more. This means that a continuous or fed batch process can be operated to produce a product which contains a high concentration of ammonium acrylate and a concentration of acrylonitrile well below the level (1,000 ppm) above which labelling for toxicity purposes is required. Thus a non-toxic ammonium acrylate product can be produced directly with no necessity for further processing. Similarly, an acrylonitrile-containing polymer can be produced and converted to a non-toxic product.

However, in the invention it is possible to use the nitrilase to convert acrylonitrile to ammonium acrylate to produce a product having a concentration of acrylonitrile greater than 1,000 ppm which can be further treated to reduce the acrylonitrile level.

We find that ammonium acrylate monomer produced by the process of the invention (bio-ammonium acrylate) shows excellent properties, equivalent to or better than the properties of monomers produced by alternative chemical routes, such as from acrylic acid derived from propylene oxide. Polymers produced using monomers made by the process of the invention also show excellent properties. The bio-ammonium acrylate made according to the invention may be converted into another chemical form, for instance acrylic acid or its sodium or other alkali metal salt or other related acrylic monomer and used as a starting monomer for the production of acrylic polymers. Alternatively it may be used without conversion, as ammonium acrylate. It may be used to form homopolymers or in combination with other monomers to produce copolymers.

We find that a further use for the novel nitrilases of the invention is in biosensors for nitrile, in particular acrylonitrile.

Thus according to a method of the invention we detect a nitrile by:

(a) contacting the nitrile with a nitrilase according to the invention, the contact being made in an aqueous environment (b) allowing conversion of the nitrile to its corresponding ammonium salt and (c) detecting a change which is related to the conversion of the nitrile.

The change may be for instance a change in conductivity in the aqueous environment. Nitriles are non-ionic species and therefore cannot be detected using conductivity measurement. If they are converted to ionic specifies, that is ammonium salts, the resulting change in conductivity can be measured. Alternatively a change in ammonium ion concentration can be detected or a system of linked enzymes can be used to detect a change.

The biosensor can be constructed in any manner conventional for sensors of this type, for instance as an electrode sensor. For instance, the nitrilase can be coated onto an electrode.

The enzyme may be present in the biosensor in an aqueous environment, for instance a liquid aqueous environment or a water-containing gel. Alternatively, the nitrile to be detected can be in an aqueous environment. It is required simply that water be present when the nitrile and nitrilase are contacted so as to allow hydrolysis to take place.

Nitrile in the vapour form can be detected using the method of the invention.

The nitrilases of the invention are particularly useful in nitrilase biosensors due to, in particular, capacity to show a substantially linear response to extremely low concentrations of nitrile.

Generally enzyme is used in the purified extracted form. However, enzyme may be used in whole cell form or as a bacterial cell fraction.

This process may be used for detecting nitrile in any environment, for instance in polymer which potentially contains unreacted acrylonitrile monomer, in effluents contaminated with nitriles in scrubbers and even in contact with acrylonitrile-containing vapours. The nitrilases of the invention can also be used to purify these discharges.

The nitrilase of the invention can be used also for removing nitrile from vapours, for instance scrubber vapours, in which nitrile can be present in very low amounts. It may be present in amounts up to 0.3 kg/m$^3$ often below 0.2 kg/m$^3$, for instance from 0.05 to 0.1 kg/ms. In the process the nitrile-containing vapour is contacted with the nitrilase and is converted to its corresponding ammonium salt, so that nitrile is reduced to below 5 mg/m$^3$, or even below 2 mg/m$^3$ (2 ppm). Contact is normally made in an aqueous environment, for instance a liquid aqueous environment or a water-containing gel, or simply with damp enzyme.

This method of the invention is particularly useful for detecting very low levels of nitrile on-line which are not detectable by other methods. In the method of the invention the nitrilase may be any nitrilase according to the invention but it is preferred that the nitrilase has a Km for the nitrile being detected of 500 $\mu$M or below, preferably 100 $\mu$M or below, more preferably 50 $\mu$M or below. Most preferably the nitrilase is one obtainable by culturing *R. rhodochrous* NCIMB 40757 or the newly deposited strain NCIMB 40833.

The following are some examples of the invention.

EXAMPLE 1

The original isolate of the strain of *Rhodococcus rhodochrous* deposited at the National Collection of Industrial and Marine Bacteria under the culture collection number NCIMB 40757 containing nitrilase enzyme or in which nitrilase enzyme can be induced is transferred into an Erlenmeyer flask containing the liquid culture medium shown in the table below.

| Component | Amount Present/liter |
|---|---|
| K$_2$HPO$_4$ | 7 g |
| KH$_2$PO$_4$ | 3 g |
| Sodium Acetate | 5 g |
| Acetonitrile | 2 g |
| MgSO$_4$.7H$_2$O | 1 g |
| CaCl$_2$.6H$_2$O | 0.2 g |
| Vitamins | 0.1 mL |
| Trace Metals | 1 mL |

The Erlenmeyer flask is incubated with agitation for 24 hours. The cells are then separated from the liquor, resuspended in 50 mM pH 7 sodium phosphate buffer and then separated from the buffer. A portion of the cells are stored frozen at −20° C. and the remainder is resuspended in 50 mM pH 7 sodium phosphate buffer containing 50 mM acrylonitrile. The specific nitrilase activity of the cells was determined to be 1060 $\mu$moles/minute/g dry weight of cells.

Similar results are obtained using the newly deposited strain NCIMB 40833.

EXAMPLE 2

The cells of the *Rhodococcus rhodochrous* strain grown as described in Example 1 are immobilised in cross-linked polyacrylamide beads as follows:

a paste consisting of cells separated from the culture medium is suspended in chilled buffer and added to a mixture of acrylamide monomer and methyl bis acrylamide (MBA) cross-linker also in chilled buffer. The water-soluble component of a redox initiator system is added immediately afterwards. The cell/monomer/initiator mixture is then transferred to a stirred resin pot containing chilled mineral oil and surfactant and the second redox initiator component, soluble in both liquid phases, is added to initiate the polymerisation. Upon polymerisation the cells are entrapped in cross-linked polymer beads.

The entrapped cells are transferred to a 50 mM pH 7 sodium phosphate buffer containing 50 mM acrylonitrile. The specific nitrilase activity of the cells was determined to be 845 $\mu$moles/minute/g dry weight cells.

EXAMPLE 3

*Rhodococcus rhodochrous* cells entrapped in cross-linked polymer beads as described in Example 2 were dried in a laboratory fluid bed drier at 60° C. to 12% moisture. Half the dried beads were then stored in an air-tight container at room temperature. The entrapped cells are transferred to 50 mM pH 7 sodium phosphate buffer containing 50 mM acrylonitrile. The specific nitrilase activity of the cells was determined to be 1038 $\mu$moles/minute/g dry weight of cells.

EXAMPLE 4

*Rhodococcus rhodochrous* cells entrapped in cross-linked polymer beads as described in Example 2 and dried in a laboratory fluid bed drier as described in Example 3 were transferred to a freeze drier and held at 0.1 mbar for 24 hours. These beads were stored in an air-tight container at room temperature.

EXAMPLE 5

The cells of the *Rhodococcus rhodochrous* strain grown as described in Example 1 were suspended in pure water at 30° C. Acrylonitrile was added periodically to the cell suspension to raise the acrylonitrile concentration to 190 mM. Samples were taken before each addition to determine the acrylonitrile, acrylamide and ammonium acrylate concentrations in the cell suspension. The table below shows the initial, maximum and final specific nitrilase activity, the final ammonium acrylate concentration and the time taken to reach that concentration.

| | |
|---|---|
| Initial specific enzyme activity ($\mu$moles/min/g) | 518 |
| Final Ammonium Acrylate concentration (M) | 5.68 |
| Time taken to reach above concentration (hours) | 6.7 |
| Maximum specific enzyme activity ($\mu$moles/min/g) | 901 |
| Specific enzyme activity upon batch completion ($\mu$moles/min/g) | 122 |

By comparison, in Appl. Microbiol. Biotechnol., Nagasawa et al., (1990), 238 mg dry weight of *Rhodococcus rhodochrous* J1 cells were incubated at 20° C. in 50 mL of 50 mM potassium phosphate buffer (pH 7.8) and 200 mM acrylonitrile. Their acrylonitrile concentration was maintained at approximately 200 mM by periodic addition of acrylonitrile. It was necessary to maintain the pH of the reaction mixture at pH 7.8 by the addition of 6M KOH solution. The table below shows the initial specific acrylonitrilase activity, the final ammonium acrylate concentration and the time taken to reach that concentration.

| | |
|---|---|
| Initial specific enzyme activity ($\mu$moles/min/g) | 2855 |
| Final Ammonium Acrylate concentration (M) | 5.44 |
| Time taken to reach above concentration (hours) | 24 |

Nagasawa et al. (1990) claimed "The accumulation of [acrylic acid with R. rhodochrous J1] was almost the same even when different concentrations of . . . cells were added. Therefore, the limitation to the accumulation [of acrylic acid with R. rhodochrous J1] can be ascribed to product inhibition and not deactivation of the enzyme". This level of product inhibition is not shown by the NCIMB 40757 enzyme.

EXAMPLE 6

The cells of the *Rhodococcus rhodochrous* strain grown as described in Example 1 were suspended in solutions of 50 mM pH 7 sodium phosphate buffer at 30° C. containing the concentrations of acrylonitrile shown in the table below. Samples were taken over time to determine the acrylonitrile, acrylamide and ammonium acrylate concentrations in the cell suspensions.

| Acrylonitrile (mM) | Specific enzyme activity ($\mu$moles/min/g) |
|---|---|
| 0.5 | 1475 |
| 0.1 | 1300 |
| 0.05 | 1023 |
| 0.025 | 717 |
| 0.015 | 583 |
| 0.01 | 395 |

From the data in the table above the Km of the nitrilase of this strain was determined to be 30.6 $\mu$M acrylonitrile.

By comparison, the table below gives the Km of two other nitrilases determined in the literature,

| Microorganism | Km ($\mu$M) | Reference |
|---|---|---|
| *Fusarium oxysporum* | 17000 | Goldlust and Bohak (1989) |
| *Rhodococcus rhodochrous* K22 | 1140 | Kobayashi et al. (1990) |

This shows the *R. rhodochrous* NCIMB 40757 nitrilase to have a far higher acrylonitrile scavenging ability than those strains previously described.

EXAMPLE 7

The cells of the *Rhodococcus rhodochrous* strain grown as described in Example 1 were suspended in solutions of 1.2 M ammonium acrylate at 30° C. containing the concentrations of acrylonitrile shown in the table below. Samples were taken over time to determine the acrylonitrile, acrylamide and ammonium acrylate concentrations in the cell suspensions.

| Acrylonitrile (mM) | Specific enzyme activity ($\mu$moles/min/g) |
|---|---|
| 0.554 | 1224 |
| 0.377 | 1383 |
| 0.322 | 743 |
| 0.183 | 656 |
| 0.079 | 499 |

From the data in the above table the apparent Km of the nitrilase of this strain in 1.2 M ammonium acrylate was determined to be 145 $\mu$M acrylonitrile. From this apparent Km value the Ki of this strain was determined to be 309 mM ammonium acrylate. This very high value shows the small level of product inhibition seen with *R. rhodochrous* NCIMB 40757 nitrilase.

This can be contrasted with the product inhibition shown by the J1 enzyme, described in Example 5 above.

EXAMPLE 8

The cells of the *Rhodococcus rhodochrous* strain grown in Example 1 were suspended in solutions of 50 mM pH 7 sodium phosphate buffer at 30° C. containing the concentrations of acrylonitrile shown in the table below. Samples were taken over time to determine the acrylonitrile, acrylamide and ammonium acrylate concentrations in the cell suspensions. The results show the relatively low levels of substrate degradation on the *R. rhodochrous* NCIMB 40757 nitrilase.

| Acrylonitrile (mM) | Specific enzyme activity ($\mu$moles/min/g) | Relative activity (%) |
|---|---|---|
| 50 | 1366 | 100 |
| 250 | 1291 | 97.8 |
| 500 | 1216 | 91.1 |

In comparison, Nagasawa et al., (1990) stated "The effect of the concentration of acrylonitrile in the reaction mixture [of *Rhodococcus rhodochrous* J1 cell suspended in 50 mM potassium phosphate buffer (pH 7.8)] on the formation rates of acrylic acid was studied [table below]. The formation rate was highest at 25–100 mM acrylonitrile. However, at concentrations higher than 200 mM, acrylonitrile caused marked inhibition. Therefore, the concentration of acrylonitrile in the reaction mixture should be kept at a concentration below 200 mM". Results of Nagasawa et al are shown in the table below.

| Acrylonitrile (mM) | Specific enzyme activity ($\mu$moles/min/g) | Relative activity (%) |
|---|---|---|
| 25 | 3630 | 99.5 |
| 50 | 3650 | 100 |
| 100 | 3610 | 98.9 |
| 200 | 3420 | 93.7 |
| 500 | 2100 | 57.5 |
| 700 | 1830 | 50.1 |

EXAMPLE 9

The cells of the *Rhodococcus rhodochrous* strain grown as described in Example 1 were suspended in solutions of 50 mM buffer at 30° C. containing the 50 mM acrylonitrile and at the pH values shown in the table below. Samples were taken over time to determine the acrylonitrile, acrylamide and ammonium acrylate concentrations in the cell suspensions.

| pH | Specific enzyme activity ($\mu$moles/min/g) |
|---|---|
| 3 | 322 |
| 4 | 611 |
| 5 | 901 |
| 6 | 1222 |
| 6.5 | 1222 |
| 7 | 1206 |
| 8 | 1186 |
| 9 | 799 |
| 9.5 | 774 |
| 10 | 0 |

This shows the maximum activity of the *R. rhodochrous* NCIMB 40757 nitrilase to be in the same pH region 6–7 which results from formation of $NH_4^+$ acrylate, obviating the need for caustic addition, compared with Nagasawa et al., (1990), who stated that the optimum pH [of *Rhodococcus rhodochrous* J1 cell suspended buffer] is 7.8.

EXAMPLE 10

The cells of the *Rhodococcus rhodochrous* strain grown as described in Example 1 were suspended in solutions of 50 mM pH 7 sodium phosphate buffer and at the temperature values shown in the table below. The cells were incubated at the temperature shown in the table below for 5 minutes prior to the addition of acrylonitrile to give a concentration of 50 mM. Samples were taken over 15 to 30 minutes to determine the acrylonitrile, acrylamide and ammonium acrylate concentrations in the cell suspension.

| Temperature (° C.) | Specific enzyme activity ($\mu$moles/min/g) |
|---|---|
| 5 | 171 |
| 10 | 269 |
| 15 | 301 |
| 20 | 628 |
| 25 | 676 |
| 30 | 1206 |
| 35 | 1671 |
| 40 | 2526 |
| 45 | 3272 |
| 50 | 4344 |
| 55 | 5256 |
| 60 | 3769 |
| 65 | 1927 |
| 70 | 257 |

Optimum activity appears to be achieved at 55° C. and high activity is retained even at 60° C. and 65° C. over 15 to 30 minutes.

in comparison, Nagasawa et al., (1990) stated "studies on the thermal stability [*Rhodococcus rhodochrous* J1 cell suspended in pH 7.8 50 mM potassium phosphate buffer] showed that the activity was stable up to 30° C., with slight inactivation between 30 and 50° C. and nearly total deactivation at 60° C.".

EXAMPLE 11 a) *Rhodococcus rhodochrous* cells entrapped in cross-linked polymer beads as described in Example 2, b) *Rhodococcus rhodochrous* cells entrapped in cross-linked polymer beads as described in Example 2 and dried in a laboratory fluid bed drier as described in Example 3 and c) *Rhodococcus rhodochrous* cells entrapped in cross-linked polymer beads as described in Example 2, dried in laboratory fluid bed drier and further dried in a freeze drier as described in Example 4 were stored in air-tight containers at room temperature for 17 days. Beads were then transferred to 50 mM pH 7 sodium phosphate buffer containing 50 mM acrylonitrile. The specific nitrilase activity of the cells in a) was determined to be 1023 $\mu$moles/minute/g dry weight of cells, in b) was determined to be 1165 $\mu$moles/minute/g dry weight of cells and in c) was determined to be 1456 $\mu$moles/minute/g dry weight of cells. This displays the remarkably high resistance of the *R. rhodochrous* sp.1290 nitrilase to immobilisation in the cellular form and subsequent drying.

EXAMPLE 12

*Rhodococcus rhodochrous* cells entrapped in cross-linked polymer beads as described in Example 2 are transferred to a fixed working volume reactor and suspended at 30° C. in ammonium acrylate at a concentration shown in the table below. Acrylonitrile is added to give the concentration shown in the table below. The nitrilase in the immobilised cells catalyses the hydrolysis of the acrylonitrile to produce ammonium acrylate. When the reactor acrylonitrile concentration is reduced to the lower concentration shown in the table below, sufficient acrylonitrile and water are added automatically to the reactor to raise the acrylonitrile concentration to the upper concentration shown in the table below. Samples were taken before each addition to determine the acrylonitrile, acrylamide and ammonium acrylate concentrations in the suspension. The initial specific nitrilase activity of the entrapped cells and the time taken for that activity to be reduced by a half was determined and is shown in the table below.

| Acrylonitrile Concentration Range (mM) | Ammonium Acrylate Concentration Range (mM) | Initial Specific enzyme activity ($\mu$moles/min/g) | Time taken for initial Specific enzyme activity to be Reduced by Half (days) |
|---|---|---|---|
| 40 to 60 | 1190 to 1210 | 573 | 48 |
| 125 to 175 | 2475 to 2525 | 850 | 7.6 |

EXAMPLE 13

Cell material was removed from the ammonium acrylate solution produced in Example 5 by centrifugation and filtration and the concentration of acrylonitrile, acrylamide and ammonium acrylate determined is shown in the table below.

| Monomer | Concentration (M) |
|---|---|
| Acrylonitrile | Below the detectable limit |
| Acrylamide | 0.023 |
| Ammonium Acrylate | 5.68 |

This shows the excellent scavenging ability of the NCIMB 40757 nitrilase for acrylonitrile and the extremely low acrylamide impurity level achievable.

EXAMPLE 14

The a) ammonium acrylate sample analysed in Example 13 above and b) an ammonia neutralised acrylic acid sample, were used to make up 20% of a monomer mixture with acrylamide to give an overall monomer concentration of 30%. Polymerisations were carried out at two different redox initiator levels and the intrinsic viscosity (IV) values of the polymers generated are shown in table below.

| Ammonium Acrylate | Initiators (ppm) | | One point IV |
|---|---|---|---|
| | t-BHP | Na$_2$SO$_3$ | (dL/g) |
| a | 2 | 4 | 24.4 |
| | 3 | 6 | 23.3 |
| b | 2 | 4 | 23.8 |
| | 3 | 6 | 23.8 |

EXAMPLE 15

Polymers generated in Example 14 above were used to flocculate a china clay suspension. No differences in the flocculant effectiveness of the polymers were detected.

We claim:

1. A nitrilase enzyme characterised in that it has Km at pH 7.0 for acrylonitrile of 500 μM or below obtainable by culturing *Rhodococcus rhodochrous* NCIMB 40757 or NCIMB 40833.

2. A nitrilase according to claim 1 having Km at pH 7.0 for acrylonitrile of 100 μM or below.

3. A nitrilase according to claim 1 having a Km at pH 7.0 for acrylonitrile of 50 μM or below.

4. A nitrilase according to claim 1 which has Ki at pH 7.0 for ammonium acrylate of at least 100 mM.

5. A nitrilase according to claim 4 having Ki at pH 7.0 for ammonium acrylate of at least 250 mM.

6. A nitrilase according to claim 1 which has a value of the ratio (Ki at pH 7.0 for ammonium acrylate)/(Km at pH 7.0 for acrylonitrile) of at least 200.

7. A nitrilase according to claim 6 having a value of the ratio at least 5000.

8. A nitrilase according to claim 1 which has at pH 6.8 an acrylonitrilase activity which is at least 80% of its acrylonitrilase activity at optimum pH.

9. A nitrilase according to claim 1 which retains at 50° C. at least 80% of its acrylonitrilase activity at 25° C.

10. A nitrilase according to claim 1 which retains at least 80% of its original acrylonitrilase specific activity after being immobilised in cross-linked polyacrylamide beads under chilled conditions as follows:

a paste consisting of cells containing nitrilase is suspended in chilled buffer and added to a mixture of acrylamide monomer and methylene bis acrylamide cross linker in chilled buffer, then the water soluble component of a redox initiator system is added immediately and the mixture is then transferred to a stirred resin pot containing chilled mineral oil and surfactant, and the second redox initiator component, soluble in both liquid phases, is added to initiate the polymerisation, upon which the cells are entrapped in cross linked polymer beads.

11. A nitrilase according to claim 10 which retains at least 90% of its immobilised acrylonitrilase specific activity after the cross-linked polyacrylamide beads are dried to 12% moisture at 60° C. and/or freeze-dried at 0.1 mbar for 24 hours.

12. A nitrilase according to claim 10 or claim 11 which retains at least 90% of its immobilised acrylonitrilase specific activity after the cross-linked polyacrylamide beads have been stored at 20° C. for 17 days.

13. A nitrilase according to claim 11 which has a half-life as measured in an aqueous solution containing 125 to 175 mM acrylonitrile and 2,475 to 2,525 mM ammonium acrylate of at least 5 days.

14. A microorganism which is *Rhodococcus rhodochrous* NCIMB 40757 or NCIMB 40833 or a mutant thereof having the ability to produce the nitrilase of claim 1.

15. A process of converting acrylonitrile to ammonium acrylate comprising introducing said acrylonitrile into a reactor in the presence as catalyst of a nitrilase according to claim 1 and in the presence of water.

* * * * *